United States Patent [19]

Gutierrez et al.

[11] Patent Number: 5,696,288

[45] Date of Patent: Dec. 9, 1997

[54] PROCESS FOR THE PREPARATION OF 2,2'-OXYDISUCCINATE

[75] Inventors: Eddie Nelson Gutierrez, Midland Park; Donna Wu, North Bergen; Shang-Ren Wu, Mahwah, all of N.J.

[73] Assignee: Lever Brothers Company, Division of Conopco, Inc., New York, N.Y.

[21] Appl. No.: 666,108

[22] Filed: Jun. 19, 1996

Related U.S. Application Data

[63] Continuation of Ser. No. 323,309, Oct. 14, 1994, abandoned.

[51] Int. Cl.[6] .................................................. C07C 59/125
[52] U.S. Cl. ................................................ 562/583
[58] Field of Search ........................................ 562/583

[56] References Cited

U.S. PATENT DOCUMENTS

| 5,030,751 | 7/1991 | Lamberti et al. | 562/583 |
| 5,068,420 | 11/1991 | Kreczmer | 562/583 |

*Primary Examiner*—Paul J. Killos
*Attorney, Agent, or Firm*—James J. Farrell

[57] ABSTRACT

A process for the preparation of 2,2'-oxydisuccinate from undissolved solid, powdered or comminuted maleate and malate species added to a slurry of alkaline earth metal hydroxide is disclosed which cooperatively controls pH, temperature, time and ratio of reactants to effectively avoid substantial phase separation.

8 Claims, No Drawings

PROCESS FOR THE PREPARATION OF 2,2'-OXYDISUCCINATE

This is a continuation application of Ser. No. 08/323,309, filed Oct. 14, 1994, now abandoned.

BACKGROUND OF THE INVENTION

1. Field of the Invention

This invention relates to the preparation of the salt of 2,2'-oxydisuccinic acid by a process which produces the salt in reasonable times and temperatures while substantially avoiding phase separation or gelation of the reaction mixture. 2,2'-oxydisuccinic acid and salts thereof are effective sequestering agents and are useful as builders in detergent compositions for household, institutional and industrial use.

2. Related Art 2,2'-oxydisuccinic acid (ODS) and salts thereof are well known and are known to have utility as sequestering agents and detergent builders. A disadvantage of ODS and its salts as detergent builders is that they may be relatively expensive to prepare.

U.S. Pat. No. 3,128,287 to Berg discloses a preparation of ODS salt by admixing maleic acid with an excess of hydroxide of calcium, barium, magnesium or strontium in the presence of water, then heating the reaction mixture from about one day to about one month at temperatures ranging from 50° C. to reflux temperatures. The process yields a mixture of malic acid and ODS. Berg's Example I teaches the preparation of ODS, wherein the aqueous mixture of maleic anhydride and calcium hydroxide is reacted at reflux (100° C.) for 4 days. Subsequently, ODS salt is isolated from the product containing ODS and malic acid salts.

U.S. Pat. No. 3,635,830 to Lamberti et al., discloses a process for the preparation of ODS based on the process of Berg. The patent teaches separation/purification of two diastereoisomeric forms of ODS obtained by the Berg process. The patent also discloses detergent compositions comprising ODS or salts thereof as detergent builders.

U.S. Pat. No. 4,798,907 to MacBrair et al. discloses an improvement in the ODS-forming processes of Berg and Lamberti et al., wherein an alkali metal hydroxide, e.g., sodium hydroxide, is incorporated into a staffing reaction mixture which also contains a divalent metal cation. To produce yields of about 80% ODS, the process generally involves reacting the mixed staffing materials in water for at least 12 hours at temperatures of about 20°–100° C. In MacBrair the amount of the divalent metal cation used is less than stoichiometric.

European Patent 206,007 to Bush teaches a process for the preparation of ODS similar to the process of the MacBrair patent. Mixtures of inorganic base with water-soluble, inorganic salts of sodium, calcium or mixtures thereof may be used. A particularly preferred reactant combination constitutes maleic acid, malic acid, calcium hydroxide and sodium hydroxide. The ODS yield of about 60% is obtained in about 6 hours.

The MacBrair et al. and Bush patents rely on incorporation of alkali metal hydroxide into the reactant mixture to minimize gelation of the mixture and to increase yields of ODS. Alkali metal hydroxides indeed produce homogeneous solutions, but unlike the alkaline earth metal hydroxides, generate higher pHs and result in a gradual decomposition of ODS under the reaction conditions employed by the MacBrair et al. and Bush patents which is believed to produce fumarate. Thus, high temperatures for long periods of time must be avoided.

U.S. Ser. No. 08/198,401 discloses methods of producing ODS by appropriate mixing of solutions of maleic acid and malic acid with selected alkaline earth metal hydroxides in selected amounts.

Improved production of ODS salts must be directed towards optimizing the process conditions in such a manner that phase separation of the reaction mixture is substantially avoided while minimizing the reaction time. There have been many different approaches to the problem of producing ODS at a lower cost. However, none has been completely satisfactory.

Accordingly, it is an object of the present invention to provide a process which produces the salt of ODS.

This and other objects and advantages will appear as the description proceeds.

SUMMARY OF THE INVENTION

The attainment of the above objects is made possible by this invention which includes a preparation of the salt of ODS by a process comprising the steps of:

(i) mixing undissolved solid, powdered or comminuted:
   (a) Maleic anhydride, maleic acid or mixtures of these; and
   (b) Malic acid including d, l and mixtures of d and l in a ratio of 1.2 to 5.0 motes of maleic species to 1.0 moles of malic species to form a first mixture;

(ii) mixing the first mixture with a slurry of alkaline earth metal hydroxide, to form a second mixture, said slurry containing a stoichiometric amount of the alkaline earth metal hydroxide, preferably $Ca(OH)_2$, to neutralize the acid species added above plus about 10% in excess of this amount, but in any case sufficient to maintain the pH of the mixture at about 11.0 to 12.3 when measured at 25° C. and 20% solids. The slurry contains sufficient water so that the mixture of solids and slurry contains at least about 40% by weight water, preferably the solids are added to the hydroxide slurry. Solid or solute loadings of up to about 60% can be achieved by the addition of solid reactants. Once the solids are added to the $Ca(OH)_2$ slurry, most of the solids go into solution. The solid malic species may also be added first followed a short time later by the maleic species.

(iii) after forming said mixture, maintaining the temperature of said mixture at about 60° C. to 95° C. for about 2 to 8 hours, optionally employing an atmosphere inert to the reactants, such as nitrogen and the like.

In general, the process involves running the reaction at a sufficient temperature for a sufficient time to form the final product while maintaining the following parameters:

A. Insuring solubility of the final ODS and other components in concentrations from about 5% up to about 45% to 60% by weight of solute by varying the temperature of reaction between about 60° C. where this higher amount of ODS and other components is substantially completely soluble up to about 95° C. where ODS and other components is only marginally soluble. Optionally, the reaction can be continued at temperatures lower than 60° C. to obtain higher yields, without encountering substantial phase separation.

B. Insuring that the solubility of the ODS and other components is never substantially exceeded at a particular temperature. This is accomplished by varying the time at which the reaction is held at that temperature to guarantee that the total concentration of ODS and other components do not substantially exceed their solubility limitations at the temperature in question. If phase separation occurs it is reversible but time consuming. The solubility of the calcium salt is important to avoid phase separation, keeping in mind the inverse nature of the calcium salt solubility, i.e., the salt is more soluble at cooler temperatures within the range. It should be noted that at low concentrations of solids, for example, concentrations of 20% then ratios of maleic to malic of less than 1.2 to 1 are sometimes employed to advantage.

Control of the molar ratio of the alkaline earth metal hydroxide to organic reactants, the ratio of maleate to malate, the amount of water in the reaction mixture and the reaction temperature of about 60° C. to 95° C. are critical to obtain the ODS salt product in about 5 hours and to avoid substantial phase separation of the reaction mixture.

In its broadest aspect, the invention provides a process for synthesizing the salt of ODS in about 5 hours at temperatures not greater than about 100° C. while substantially avoiding phase separation of the reaction mixture.

An alkaline earth metal salt of ODS may be isolated from other organic species contained in the reaction product obtained by the inventive process and converted to ODS acid (Formula I below)

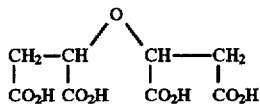

FORMULA I or ODS salts such as monovalent cation salts, ammonium salts, morpholinium salts, alkanol ammonium salts and mixtures thereof, by methods known in the art. Such methods are disclosed, for example, in U.S. Pat. No. 3,128,287 to Berg and U.S. Pat. No. 3,635,830 to Lamberti et al. discussed above and incorporated herein by reference. As noted, the U.S. Pat. No. 3,635,830 patent also discloses detergent compositions containing ODS or salts thereof.

In defining the ODS salt forming process of this invention it is intended to include both batch and continuous processes.

DETAILED DESCRIPTION OF THE INVENTION

The inventive process of this invention for obtaining the reaction product which contains the salt of ODS and in which gelation of the reaction mixture is substantially avoided is outlined as follows:

(i) adding solid comminuted or powdered
  (a) Maleic anhydride, maleic acid or mixtures of these; and
  (b) Malic acid including d, l, and mixtures of d and l, in a ratio of 1.2 to 5.0 moles of maleic species to 1.0 moles of malic species to form a first mixture;

(ii) mixing the first mixture with a slurry of alkaline earth metal hydroxide, to form a second mixture, said slurry containing a stoichiometric amount of the alkaline earth metal hydroxide, preferably Ca(OH)$_2$ to neutralize the acid species added above plus about 10% in excess of this amount, but in any case sufficient to maintain the pH of the mixture at about 11.0 to 12.3 when measured at 25° C. and 20% solids, said slurry containing sufficient water so that the mixture of solids contains at least about 45% by weight water, preferably the solids or mixture added to the hydroxide slurry. Once the said solids are added to the calcium hydroxide, slurry the acid solids and the excess calcium hydroxide go into solution;

(iii) after forming said mixture, maintaining the temperature of said mixture preferably at about 60° C. to 95° C.

for about 2 to 8 hours, optionally employing an atmosphere inert to the reactants such as nitrogen and the like.

The process of this invention for the preparation of the salt of ODS includes forming an aqueous mixture of staffing reactants containing a malate moiety, a maleate moiety and an alkaline earth metal hydroxide. The chemically suitable forms of malate and maleate reactants include acids and the anhydride of maleic acid. The molar ratio of maleate to malate is about 5.0:1 to about 1.2:1.

The alkaline earth metal hydroxide in the reaction mixtures of the inventive process is selected from the group consisting of barium hydroxide, strontium hydroxide or calcium hydroxide. The most preferred alkaline earth metal hydroxide for use in this invention is calcium hydroxide.

The ODS salt forming reaction of the present invention is conducted at high concentration in aqueous media to afford efficacy and high throughput. The amount of water present may vary and is preferably sufficient to permit the reaction to proceed with the amount of water being about 40% to 95%. The amount may, however, be more or less depending on design parameters.

Desirably, the reactants of the staffing mixture for the process are combined in water using physical agitation. In the preferred embodiments of the invention, the alkaline earth metal hydroxide slurry is mixed with a solid or powdered mixture of the malate and maleate moieties producing what is believed to be a soluble mixed calcium complex. The stability of this calcium salt mixture is dependent on the temperature and pH. It is believed that it is necessary to form this complex to achieve high yields of ODS. If the hydroxide is first mixed with maleate in the absence of malate, or malate in the absence of maleate, insoluble calcium maleate and calcium malate are produced which when mixed together produce an insoluble mixture and poor yields of ODS will usually be obtained. The reaction is carried out in an apparatus equipped with stirring means, e.g., on a laboratory scale, a mechanical stirring device is employed. The apparatus may also be equipped with a condenser to provide some means of condensing water which evaporates, so that it returns to the reaction mixture. The reaction is conducted at atmospheric pressure.

The reaction temperature for the process ranges from about 60° C. to about 95° C., preferably from about 70° C. to about 90° C. To minimize phase separation the reaction temperature is maintained for at least about 2 hours and preferably no longer than about 8 hours at temperatures ranging from 60° C. to 95° C. The aqueous reaction product typically contains a mixture of 2,2'-oxydisuccinate, malate, maleate and fumarate. Optionally the reaction can be continued at temperature lower than about 60° C. to obtain higher yields, without encountering substantial phase separation.

Maleic acid either R or S forms can be employed to produce RR and RS or SS and RS forms in a highly stereospecific synthesis of ODS.

The reaction products obtained by the processes of this invention contain the alkaline earth metal salt of ODS and may be worked up by methods known in the art. Generally, the work up comprises the steps of reduction of calcium content in the product mixture and acidification or conversion into monovalent cation salts, ammonium salts, morpholinium salts, alkanol ammonium salts and mixtures thereof.

The calcium content of the reaction products may be reduced by conventional means. Removal of calcium can be carried out in a number of ways known in the art. In general, simply adding a calcium precipitating material will suffice. Such calcium precipitating materials include alkali metal carbonate, pyrophosphate, sulfates, bicarbonate and/or alkali metal silicate and mixtures thereof, for example, the addition of sodium carbonate will convert the alkaline earth metal salt obtained to the sodium salt. The resulting calcium precipitate can thereafter be removed from the aqueous reaction product mixture by filtration. In an alternative mode, removing calcium from the aqueous reaction product mixtures involves treatment of said mixtures with an appropriate insoluble ion exchange resin or zeolite. No matter what technique is employed, the calcium content of the ODS salt prepared by methods herein should desirably be reduced to the extent that calcium is present in an amount of no more than about 1.0% of the ODS salt and preferably less than 0.2%, in order to form compositions particularly suitable as detergent builders. This can be accomplished by the method of defensive publication T 101,805.

ODS salts formed herein can also be treated, after calcium removal, in a further step, using organic or aqueous solvent extraction to remove excess reactants, such as maleates, or organic reaction by-products, such as fumarates. This can, for example, be accomplished by conventional salt separation procedures using a solvent such as a mixture of methanol and water (4:1 v/v) in which these excess reactants and reaction by-products are relatively soluble and in which the desired ODS salt is relatively insoluble as disclosed in U.S. Pat. No. 5,068,420.

At any stage after the ODS salt formation, and after reducing the calcium salt content the reaction product can be concentrated by removal of water to the desired extent. Water removal can, for example, after calcium removal, involve substantially complete drying of the reaction product mixture, e.g., by spray drying, so that the ODS salt is recovered in solid, e.g., granular, form. The sodium salt of ODS in the form of aqueous liquid may be utilized directly in the preparation of detergent compositions or laundry additive products of the types more fully described hereinafter.

It is possible, if desired, to acidify the product mixtures using conventional acidification or ion exchange techniques to convert the ODS salts therein to their free acid form. Normally, however, the ODS materials of this invention can, after calcium depletion or complete replacement by sodium, be used as builders in their water-soluble salt form, and such acidification is therefore not usually necessary or desirable.

When converted into suitable form, the ODS salts can be used as sequestering builders in a wide variety of detergent or laundry additive compositions.

Detergent compositions incorporating the ODS salt prepared using the processes of this invention contain as essential components from about 0.5% to about 98% of a surfactant and from about 2% to about 99.5% of the ODS compounds as a detergency builder, generally in sodium-salt form. Surfactants that are useful in the present invention are the anionic (soap and nonsoap), nonionic zwitterionic and ampholytic compounds. The chemical nature of these detergent compounds is not an essential feature of the present invention. Moreover, such detergent compounds are well known to those skilled in the detergent art and the patent and printed literature are replete with disclosures of such compounds. Typical of such literature are "Surface Active Agents" by Schwartz and Perry and Berch, the disclosures of which are incorporated by reference herein. The ODS builder can be used either as the sole builder or where desired can be used in conjunction with other well-known builders, examples of which include water-soluble salts of phosphates, pyrophosphates, orthophosphates, polyphosphates, phosphonates, carbonates, polyhydroxysulfonates, polyacetates, carboxylates, polycarboxylates, succinates and the like.

In addition to the surfactant and builder there may be optionally present additional ingredients which enhance the performance of the detergent composition. Typical examples thereof include the well known soil suspending agents, hydrotropes, corrosion inhibitors, dyes, perfumes fillers, optical brighteners, enzymes, suds boosters, suds depressants, germicides, anti-tarnishing agents, cationic detergents, softeners, bleaches, buffers and the like.

The detergent compositions of the present invention may be in any of the usual physical forms for such compositions, such as powders, beads, flakes, bars, tablets, noodles, liquids, pastes and the like. The detergent compositions are prepared and utilized in the conventional manner. The wash solutions thereof desirably have a pH from about 7 to about 12, preferably from bout 9 to about 11.

In addition to their utility as builders in detergent and laundry additive compositions, the ODS salts of the invention can, after reducing their calcium content, also be utilized in other contexts wherein water hardness sequestration is required. Other uses are provided in water softening compositions, devices and methods and boiler descaling compositions and methods. It is also theorized that ODS can complex heavy metals which react with bleach and thus can stabilize bleach.

It should also be noted that when ODS is employed as the free acid or as partly neutralized salt it has utility in metal cleaning composition under pH conditions of about 2 to about 5. The following examples are designed to illustrate, but not to limit, the practice of the instant invention. All percentages and parts herein are by weight unless indicated otherwise. All ratios herein are mole ratios unless indicated otherwise. R,S-malic acid is used in the Examples unless indicated otherwise.

Reaction mixture samples and reaction products were analyzed by HPLC and/or NMR. The HPLC analysis is carried out using a Hitachi instrument. The mobile phase is a 30/70 acetonitrile/water mixture with 0.75 g/l of 85% phosphoric acid at a pH of about 3 to 4. The column is an RP/SAX Regis 25 cm×4.6 mm in dimension. The flow rate is 1.5 ml/minute. The wavelength at which the detector is set is 210 nm. Samples are diluted with the mobile phase. Quantification is done using an external standard. The volume of the injections used are 50 μL.

The NMR is a 200 MHz Bruker model. Samples are prepared by ion exchanging the calcium salts, followed by neutralization of the acids with sodium carbonate, drying, and dissolution in $D_2O$. Peak assignments are as follows:

Fumaric 6.28 δ

Maleic 5.78 δ

Malic CH 4.1 to 4.3 δ

$CH_2$ 2.0 to 2.5 δ (overlap with ODS)

ODS CH 3.83 to 3.59 δ

$CH_2$ 2.0 to 2.5 δ (overlap with malic)

EXAMPLE 1

A dry mix of maleic acid, 39.4 g (0.33 mole), and malic acid, 38 g (0.28 mole) are added slowly to a 250 ml three neck flask equipped with over head stirrer, nitrogen gas inlet and thermometer containing 50.3 g (0.68 mole) calcium hydroxide in 83 ml water. The mixture is stirred at 200 rpm to prevent the formation of fish-eyes. The initial temperature is 25° C. and rapidly rises to 50° C. during the rest of the addition. The temperature is maintained at 68° C. for 3.5 hours, at 35° C. for 20 hours and then at 35° C. for an additional 46 hours. Weight % calculated by NMR.

| Reactants (mole ratio) | | | | Total Reaction Time | Products (wt. %) NMR | | | |
|---|---|---|---|---|---|---|---|---|
| Maleic | Malic | Ca(OH)$_2$ | Solids % | Hours | ODS | Malic | Maleic | Fumaric |
| 1.2 | 1 | 2.5 | 50 | 3.5 | 73 | 13 | 14 | — |
| | | | | 23.5 | 86 | 6 | 8 | — |
| | | | | 69.5 | 90 | 5 | 5 | — |

EXAMPLE 2

A dry mix of maleic acid, 32.4 g (0.28 mole), and malic acid, 30.8 g (0.23 mole) are added slowly to a 250 ml three neck flask equipped with overhead stirrer, nitrogen gas inlet and thermometer containing 41.4 g (0.54 mole) calcium hydroxide in 111.2 ml water. The mixture is stirred at 200 rpm to prevent the formation of fish-eyes. The initial temperature is 25° C. and rapidly rises to 50° C. during the rest of the addition. The temperature is maintained at 65° C. for 2 hours and at 45° C. for 16 hours. Weight % calculated by NMR.

| Reactants (mole ratio) | | | | Total Reaction Time | Products (wt. %) NMR | | | |
|---|---|---|---|---|---|---|---|---|
| Maleic | Malic | Ca(OH)$_2$ | Solids % | Hours | ODS | Malic | Maleic | Fumaric |
| 1.2 | 1 | 2.5 | 40 | 18 | 87 | 5 | 8 | — |

EXAMPLES 3 and 4

A dry mix of maleic acid, 29 g (0.25 mole), and R- or S-malic, 28 g (0.21 mole) are added slowly to a 250 ml three neck flask equipped with overhead stirrer, nitrogen gas inlet and thermometer containing Ca(OH)$_2$, 37.7 g (0.51 mole) and 128.6 ml of water while the temperature is maintained at 30°–40° C. The temperature is mtained at 35° C. for 28 hours. The weight % is by NMR.

| Reactants (mole ratio) | | | | | Total Reaction Time | Products (wt. %) NMR | | | |
|---|---|---|---|---|---|---|---|---|---|
| | Malic | | | | | | | | |
| Maleic | R | S | Ca(OH)$_2$ | Solids % | Hours | ODS | Malic | Maleic | Fumaric |
| 1.2 | 1 | — | 2.5 | 35 | 28 | 88 (RR & RS) | 5 | 7 | — |
| 1.2 | — | 1 | 2.5 | 35 | 28 | 92 (SS & RS) | 3 | 5 | — |

EXAMPLE 5

Malic acid, 30.8 g (0.23 mole) is added gradually to a 250 ml three neck flask containing calcium hydroxide, 41.4 g (0.54 mole) and 111 ml water. After 2–3 minutes, maleic acid, 32.4 g (0.28 mole), is added while the temperature is maintained below 55° C. At this point the mixture is opaque. The reaction temperature is maintained at 60° C. for 24 hours. Upon cooling, the opaque mixture solidifies. Weight % calculated by NMR.

| Reactants (mole ratio) | | | | Total Reaction Time | Products (wt. %) NMR | | | |
|---|---|---|---|---|---|---|---|---|
| Maleic | Malic | Ca(OH)$_2$ | Solids % | Hours | ODS | Malic | Maleic | Fumaric |
| 1.2 | 1 | 2.5 | 40 | 24 | 71.8 | 16.9 | 4.9 | 6.3 |

It is understood that the examples and embodiments described herein are for illustrative purposes only and that various modification or changes in the light thereof will be suggested to persons skilled in the art and are to be included within the spirit and purview of this application and the scope of the appended claims.

What is claimed is:

1. A process for preparing 2,2'-oxydisuccinic acid comprising:

(i) mixing undissolved solid, powdered or comminuted:
   a) maleic anhydride, maleic acid or mixtures of these; and
   b) malic acid selected from the group including d-malic acid, l-malic acid and mixtures of these, in a ratio of 1.2 to 5.0 moles of maleic species to 1.0 moles of malic species to form a first mixture;

(ii) mixing the first mixture with a slurry of alkaline earth metal hydroxide, to form a second mixture, said slurry containing a stoichiometric amount of alkaline earth metal hydroxide to neutralize said acid plus about 10% in excess of said amount the total amount of said alkaline earth metal hydroxide being sufficient to maintain the pH of said mixture at about 11.0 to 12.3 when measured at 25° C. and 20% solids, said slurry containing sufficient water so that said second mixture contains at least about 40% by weight water;

(iii) after forming said second mixture, maintaining the temperature of said second mixture at about 60° C. to 95 ° C. for about 2 to 8 hours, optionally employing an inert atmosphere.

2. A process as defined in claim 1 wherein the reaction is extended for a period of about 24 hours at a temperature of less than 60° C.

3. A process as defined in claim 1 wherein the alkaline earth metal hydroxide is calcium hydroxide.

4. A process as defined in claim 1 wherein the mole ratio of said a) to said b) is 1.2 to 1.

5. A process as defined in claim 1 wherein the 2,2'-oxydisuccinic acid is recovered from the reaction mixture.

6. A process as defined in claim 1 wherein the total concentration of maleic, malic and calcium species at the beginning of the reaction is about 5% to 60%.

7. A process as defined in claim 1 wherein the total concentration of maleic, malic and calcium species at the beginning of the reaction is about 40% to 50%.

8. A process as defined in claim 1 wherein said process is stereospecific based on the stereospecificity of the starting material.

* * * * *